(12) United States Patent
Klocke et al.

(10) Patent No.: US 9,017,398 B2
(45) Date of Patent: Apr. 28, 2015

(54) ABLUMINALLY COATED DRUG-ELUTING STENTS HAVING A FORM-FITTING PROTECTIVE LAYER

(75) Inventors: Bjoern Klocke, Zurich (CH); Claus Harder, Uttenreuth (DE); Alexander Borck, Aurachtal (DE)

(73) Assignee: Biotronik AG, Buelach (CH)

( * ) Notice: Subject to any disclaimer, the term of this patent is extended or adjusted under 35 U.S.C. 154(b) by 340 days.

(21) Appl. No.: 13/177,865

(22) Filed: Jul. 7, 2011

(65) Prior Publication Data

US 2012/0016466 A1    Jan. 19, 2012

Related U.S. Application Data

(60) Provisional application No. 61/364,817, filed on Jul. 16, 2010.

(51) Int. Cl.
| | |
|---|---|
| *A61L 27/14* | (2006.01) |
| *A61L 31/16* | (2006.01) |
| *A61L 31/04* | (2006.01) |
| *A61L 31/02* | (2006.01) |
| *A61L 31/10* | (2006.01) |
| *A61L 31/14* | (2006.01) |

(52) U.S. Cl.
CPC .............. *A61L 31/16* (2013.01); *A61L 31/045* (2013.01); *A61L 31/022* (2013.01); *A61L 31/10* (2013.01); *A61L 31/148* (2013.01); *A61L 2420/08* (2013.01)

(58) Field of Classification Search
CPC ... A61L 27/34; A61L 27/222; A61L 2420/08; A61L 31/045; A61L 31/148; A61L 31/16
USPC ........... 623/1.38, 1.39, 1.42, 1.43, 1.44, 1.45, 623/1.46, 1.47, 1.48
See application file for complete search history.

(56) References Cited

U.S. PATENT DOCUMENTS

| | | | |
|---|---|---|---|
| 2003/0083740 A1* | 5/2003 | Pathak | 623/1.43 |
| 2005/0229264 A1* | 10/2005 | Chang et al. | 435/325 |
| 2008/0058923 A1* | 3/2008 | Bertsch et al. | 623/1.46 |
| 2008/0147177 A1* | 6/2008 | Scheuermann et al. | 623/1.42 |

FOREIGN PATENT DOCUMENTS

WO          03037223 A1      5/2003

OTHER PUBLICATIONS

EP11172366.4 European Search Report mailed Sep. 25, 2014.

* cited by examiner

*Primary Examiner* — David Isabella
*Assistant Examiner* — Suba Ganesan
(74) *Attorney, Agent, or Firm* — Wagenknecht IP Law Group PC

(57) ABSTRACT

A drug-eluting stent, comprising a base body that is made of an implant material, the base body being partially or entirely covered on the abluminal side with an active ingredient-releasing coating that comprises or is made of a polymer and an active ingredient having an antiproliferative effect, characterized in that the stent's luminal surface and the abluminal surface carrying the active ingredient-releasing coating are covered by a biocorrodible protective layer in a form-fitting manner.

18 Claims, 2 Drawing Sheets

ABLUMINALLY COATED DRUG-ELUTING STENTS HAVING A FORM-FITTING PROTECTIVE LAYER

CROSS REFERENCE TO RELATED APPLICATIONS

This invention claims benefit of priority to U.S. patent application Ser. No. 61/364,817 filed on Jul. 16, 2010; the contents of which are herein incorporated by reference in their entirety.

TECHNICAL FIELD

The invention relates to a stent for implantation.

BACKGROUND

The implantation of stents has become established as one of the most effective therapeutic measures for the treatment of vascular diseases. Stents have the purpose of performing a stabilizing function in hollow organs of a patient. For this purpose, stents featuring conventional designs have a filigree supporting structure comprising metal braces, which is initially present in a compressed ("crimped") form for introduction into the body and is expanded at the site of the application. One of the main application areas of such stents is to permanently or temporarily dilate and hold open vascular constrictions, particularly constrictions (stenoses) of the coronary blood vessels. In addition, aneurysm stents are also known, which are used to support damaged vessel walls.

Stents comprise a typically tubular base body having sufficient load-bearing capacity in order to hold the constricted vessel open to the desired extent, with the blood flow continuing without impairment through the lumen thereof. This base body is generally formed by a lattice-like supporting structure, which is composed of struts and allows the stent to be introduced in a compressed state, in which it has a small outside diameter, all the way to the stenosis of the particular vessel to be treated and to be expanded there, for example by way of a balloon catheter, so that the vessel has the desired, enlarged inside diameter.

The stent has a base body made of an implant material. An implant material is a non-living material, which is used for applications in medicine and interacts with biological systems. A basic prerequisite for the use of a material as implant material, which is in contact with the surrounding body area when used as intended, is the body friendliness thereof (biocompatibility). Biocompatibility shall be understood as the ability of a material to evoke an appropriate tissue response in a specific application. This includes an adaptation of the chemical, physical, biological, and morphological surface properties of an implant to the recipient's tissue with the aim of a clinically desirable interaction. The biocompatibility of the implant material is also dependent on the temporal course of the response of the biosystem in which it is implanted. For example, irritations and inflammations occur in a relatively short time, which can lead to tissue changes. As a function of the properties of the implant material, biological systems thus react in different ways. According to the response of the biosystem, the implant materials can be divided into bioactive, bioinert and degradable/resorbable materials.

Implant materials for stents comprise polymers, metallic materials, and ceramic materials (as coatings, for example). Biocompatible metals and metal alloys for permanent implants comprise, for example, stainless steels (such as 316L), cobalt-based alloys (such as CoCrMo cast alloys, CoCrMo forge alloys, CoCrWNi forge alloys and CoCrNiMo forge alloys), technical pure titanium and titanium alloys (such as cp titanium, TiAl6V4 or TiAl6Nb7) and gold alloys. In the field of biocorrodible stents, the use of magnesium or technical pure iron as well as biocorrodible base alloys of the elements magnesium, iron, zinc, molybdenum, and tungsten are proposed.

A biological reaction to polymeric, ceramic or metallic implant materials depends on the concentration, exposure time, and manner in which they are administered. Frequently, the presence of an implant material leads to inflammatory reactions, the trigger of which can be mechanical stimuli, chemical substances, or metabolites.

A key problem of stenting into blood vessels is restenosis as a result of excessive neointimal growth, for example, which is caused by a strong proliferation of the surrounding arterial smooth muscle cells and/or a chronic inflammation reaction. As an alternative or in addition, restenosis can be caused and/or promoted by the physiological effect of releasing the decomposition products of the stent, particularly the biocorrodible stent. For example, the decomposition of magnesium-containing stents creates an alkaline environment, which may result in increased muscular tension of the surrounding vascular muscle. As a result of such increased muscular tension, the cross-section of the stent may decrease or the stent integrity may even be lost prematurely.

Strategies to prevent restenosis focus, for example, on inhibiting the proliferation of surrounding cells through medication, such as by the treatment with active ingredients having an antiproliferative effect (such as cytostatic drugs). The active ingredients can be provided, for example, on the implant surface in the form of a coating. Active ingredients that have to already been proposed or employed in this context are sirolimus or derivatives thereof, or taxanes, such as paclitaxel, or salts thereof.

For use, the stent is typically provided with an active ingredient-releasing coating, wherein it has been found that stents comprising the active ingredient-releasing coating exclusively on the abluminal side of the stent are superior to those stents comprising the active ingredient-carrying coating also on the luminal side.

One problem of such stents having in particular only an abluminal active ingredient-releasing coating (referred to as "drug-eluting stents" or DES) is that part of the active ingredient-releasing coating is uncontrollably lost as a result of the mechanical stress that occurs during crimping and the subsequent dilation at the target site. On the one hand, this causes the quantity of the active ingredient that is in fact available at the target site for use is very difficult to predict, thereby creating the possibility of underdosing. On the other hand, the active ingredients that are employed are active ingredients that have significant potential for side effects, which when applied to an unintended site or released systematically in high volume may have a negative impact on the patient being treated.

SUMMARY

It is the object of the present invention to reduce or prevent at least one of the disadvantages of the prior art, This object is achieved by providing a drug-eluting stent comprising a base body that is made of an implant material, on the abluminal side the base body being covered partially or entirely with an active ingredient-releasing coating, which comprises or is made of a polymer and an active ingredient having an antiproliferative effect, characterized in that the stent's luminal surface and the abluminal surface (carrying the active ingredient-releasing coating) are covered by a biocorrodible protective layer in a form-fitting manner.

The stent according to the invention preferably comprises the active ingredient-releasing coating exclusively on the abluminal side of the base body.

The present invention is based on the finding that a premature detachment of the active ingredient-carrying coating from the base body of the stent can be prevented particularly effectively in that the entire base body, including the active ingredient-carrying coating, is coated both on the luminal and the abluminal side with a biocorrodible protective layer covering the stent in a form-fitting manner. As a result of this protective layer, damage or premature detachment of the active ingredient-carrying coating prior to and/or during implantation is prevented. The protective layer protects the layers and components underneath from mechanical stress, for example. Since the protective layer as such is biocorrodible, it is ensured that the protective layer degrades quickly by biocorrosion after implantation, whereby the active ingredient-carrying coating is exposed. The active ingredient-carrying coating can then exhibit the inherent release behavior thereof. In the stent according to the invention it is therefore ensured that the active ingredient-carrying coating cannot detach uncontrollably from the stent. In this way, a defined quantity of active ingredient can be provided and released in the desired manner at the intended site of action.

The stent according to the invention preferably comprises a base body made of a metallic implant material. The base body of the stent can in particular be entirely or partially made of or comprise a biocorrodible metallic material. The metallic base body is in particular made of magnesium, a biocorrodible magnesium alloy, technical pure iron, a biocorrodible iron alloy, a biocorrodible tungsten alloy, a biocorrodible zinc alloy, or a biocorrodible molybdenum alloy. It is particularly preferred when the biocorrodible metallic material is a magnesium alloy. In the present invention, a magnesium alloy, iron alloy, zinc alloy, molybdenum alloy, or tungsten alloy denotes a metallic structure comprising magnesium, iron, zinc, molybdenum or tungsten as the main constituent. The main constituent is the alloying constituent, the weight ratio of which is the highest in the alloy. The proportion of the main constituent is preferably more than 50% by weight, particularly more than 70% by weight. The alloy is to be selected in the composition thereof such that it is biocorrodible.

The stent according to the invention comprises an active ingredient-releasing coating on parts of or the entire abluminal surface of the base body. A coating or layer as defined by the invention denotes an application of the constituents of the coating or of the layer onto at least some sections of the base body of the stent. A coating or layer thickness preferably ranges from 1 nm to 100 µm, with 300 nm to 15 µm being particularly preferred. The active ingredient-releasing coating can be applied directly and preferably exclusively to parts of or to the entire abluminal surface of the base body. In addition, the strut flanks (strut sides) may also carry a coating. The processing can be carried out according to standard coating methods. Limiting the active ingredient-releasing coating to the abluminal side of the base body can be achieved, for example, in that the luminal side is protected by shading when applying the coating. Further abluminal coatings by way of pipetting methods are known to the person skilled in the art. It is possible to produce single-layer or multi-layer systems. The active ingredient-releasing coating can be applied directly onto the base body of the stent. However, it is also possible to provide further additional, optionally adhesion promoting layers in between, such as one or more parylene-containing layers.

The active ingredient-releasing coating comprises or is made of a polymer and an active ingredient having an antiproliferative effect. The active ingredient having an antiproliferative effect can be understood as being an individual active ingredient or a mixture comprising a plurality of different active ingredients. Suitable active ingredients are known to the person skilled in the art. In addition to the active ingredient, the coating may comprise further compounds or adjuvants, such as substances for controlling the release, preserving and/or stabilizing the active ingredient. Advantageously, the active ingredient may comprise sirolimus or a derivative thereof, or a taxane or a salt thereof. Active ingredients that act on mTOR are particularly advantageous, as are RAS inhibitors, in particular such preventing RAS adhesion. For the purpose of the present invention, the term "taxane" shall denote chemical compounds that have a diterpene-containing skeleton and exhibit a cytotoxic or cytostatic activity. Preferred taxanes are those used for cancer therapy and comprise paclitaxel, docetaxel, larotaxel, ortataxel and/or tesetaxel, and the salts and/or derivatives thereof. In a particularly preferred embodiment, the taxane is paclitaxel and/or salts thereof.

The active ingredient-releasing coating comprises a non-degradable or preferably a degradable polymer. The person skilled in the art knows suitable polymers and polymer/active ingredient combinations having a suitable release profile. In a preferred embodiment, the polymer of the active ingredient-releasing coating comprises a polymer or copolymer selected from the group consisting of PLGA, PLLA, PVP/PVA copolymers, in particular PVP/PVA copolymers having a weight ratio of PVP to PVA of 20:80 to 70:30, preferably a weight ratio of PVP to PVA of 20:80, vinyl acetate/crotonic acid copolymers, a terpolymer comprising the monomers vinyl acetate, vinyl propionate and crotonic acid, methyl vinyl ether/maleic acid anhydride copolymers, acrylate resins, copolymers made of PVP and dimethylamino ethyl acrylate, and pure polymers made of the monomers of the above polymers or copolymers.

The surface of the luminal side of the base body of the stent according to the invention can be partially or entirely structured, so that, for example, the endothelialization of the luminal surface is favored, and optionally accelerated, after the biocorrodible protective layer has degraded.

The stent according to the invention is characterized in that both the luminal surface of the base body and the abluminal surface of the base body carrying the active ingredient-releasing coating are entirely and form-fittingly covered with the biocorrodible protective layer. The biocorrodible protective layer forms the uppermost layer of the stent according to the invention. For the purpose of the present invention, the "uppermost layer" shall be understood as the layer of the stent which, after implantation, either comes closest to, or preferably even has direct contact with, either the vascular wall (abluminal side) or the blood that is flowing (luminal side).

The biocorrodible protective layer covers the luminal and abluminal surfaces of the base body of the stent in a form-fitting manner. Form-fitting coverage shall mean that the biocorrodible protective layer substantially shields the luminal and abluminal surfaces of the stent from the surroundings. The form fit exists in particular in all directions of the planes that are perpendicular to the cylinder axis of the stent. The layer constitutes mechanical protection (protective layer).

Biocorrodibility as defined by the present invention shall mean that, after implantation, the protective layer reacts at the implantation site with the surroundings due to biological or biochemical interaction and is degraded.

According to the invention, layers, substances, materials, alloys, and elements are referred to as biocorrodible when in the physiological environment thereof degradation or a reaction takes place, so that a shaped body made of the material is no longer present in its entirety, or at least predominantly. A possible test medium for testing the corrosion behavior of a potential material is synthetic plasma, as that which is required according to EN ISO 10993-15:2000 for biocorrosion analyses (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l). For this purpose, a sample of the materials to be analyzed is stored in a closed sample container with a defined quantity of the test medium at 37° C. The samples are removed at intervals—which are adapted to the anticipated corrosion behavior—ranging from a few hours to several months and analyzed for traces of corrosion in the known manner. The synthetic plasma according to EN ISO 10993-15:2000 corresponds to a blood-like medium and thus is a possible medium to reproducibly simulate a physiological environment as defined by the invention. A substance is referred to as biocorrodible, for example, when the substance has corroded or reacted more than 50% in the above test at the latest after a period 6 months.

In a preferred embodiment, the protective layer can biocorrode within a very short period. The fast biocorrodibility of the protective layer ensures that the active ingredient-releasing coating becomes accessible as quickly as possible after implantation and can exhibit the desired release behavior. In a particularly preferred embodiment, the protective layer is characterized in that it has corroded at least 50% within a period of 1 day and 6 months. The temporal dependencies between the degradable protective layer and degradable carrier are described as follows (ta<=tb, tb<=5 years, preferably 6 months).

In a further preferred embodiment, the biocorrodible protective layer is designed such that it is pervious to the active ingredient of the active ingredient-releasing coating. In this way, it can be ensured that the active ingredient can already be released during the corrosion phase of the protective layer, whereby a delay in the release of the active ingredient is prevented.

The biocorrodible protective layer is preferably free of active ingredients. In a particular embodiment, the biocorrodible protective layer may, however, comprise a second active ingredient, wherein this second active ingredient preferably has no negative effect (such as an antiproliferative effect) on endothelial cells. The second active ingredient can be, in particular, an active ingredient that promotes post-implantation stent healing.

The biocorrodible protective layer, for example, may comprise or be made of a biocorrodible polymer, a biocorrodible saccharide, or a biocorrodible gelatin.

In a preferred embodiment, the biocorrodible layer may comprise or be made of a short-chained PLGA polymer having 50% to 65% PLA monomer units and 35% to 50% PGA monomer units. The iv values are 0.15-0.94 dl/g (in HFIP: 0.1%; 25° C.), preferably 0.3-0.5 dl/g, in accordance with a mean molar mass of approximately 15,000-25,000 Da. In particular a short-chained PLGA polymer may be used, which comprises the monomers PLA and PGA in a weight ratio of 50:50 and has a mean molar mass of 20,000 Da.

In another preferred embodiment, the biocorrodible protective layer may comprise or be made of high bloom gelatin, average bloom gelatin, or a mixture thereof. The gelatin constituents preferably account for 1 to 20% by weight of the biocorrodible protective layer, with 5 to 10% by weight being particularly preferred, wherein the information in % by weight is relative to the total weight of the biocorrodible protective layer.

One advantage that is associated with the use of gelatin is that gelatin or a gelatin mixture having a congealing point that is at a temperature below the body temperature can be used. In this way, the biocorrodible protective layer remains intact and strong as long as the congealing temperature is not exceeded. After implantation, the stent, and with it the protective layer, slowly heats up to the body temperature, the congealing temperature is thereby exceeded and the gelatin layer starts to liquefy.

The biocorrodible protective layer may comprise or be made of a gelatin mixture, wherein the gelatin constituents of the gelatin mixture account for 10-90% by weight high bloom gelatin having a gel strength of 250 bloom and 90-10% by weight average bloom gelatin having a gel strength of ≥50 to <250 bloom, wherein the information in % by weight is relative to the total weight of the gelatin constituents of the gelatin mixture. The % by weight of high bloom gelatin and the % by weight of average bloom gelatin in total preferably always amount to 100% of the total weight of the gelatin components of the gelatin mixture. The high bloom gelatin can have a gel strength of ≥250 to 400 bloom, preferably from ≥250 up to and including 300 bloom.

"Bloom" denotes the unit of the gel strength of gelatin. The indicator describes the weight in grams needed to depress the surface of 112 grams of 6.67% (w/w) gelatin 4 mm deep when using a plunger measuring 0.5 inches in diameter. The higher the gel strength of the gelatin, to the higher is the bloom value. The bloom is determined under standardized conditions at +10° C., wherein the gelatin specimen to be tested is previously matured for 17 hours at +10° C. In order to determine the bloom, a Bloom gellometer may be used.

The gelatin constituents of the gelatin mixture of the biocorrodible protective layer of the stent according to the invention, for example, can account for 25 to 75% by weight high bloom gelatin and 75 to 25% by weight average bloom gelatin, preferably 40 to 60% by weight high bloom gelatin and 60 to 40% by weight average bloom gelatin, with 50% by weight high bloom gelatin and 50% by weight average bloom gelatin being particularly preferred, wherein the information in % by weight in each case is relative to the total weight of the gelatin constituents of the gelatin mixture.

Gelatin is a mixture of polypeptides, depending on the production having molar weights of approximately 13,500 to 500,000 g/mol (determined by SDS gel electrophoresis or gel chromatography), which is obtained by the hydrolysis of collagen. The amino acid composition largely corresponds to that of the collagen from which it was produced and, with the exception of tryptophan and methionine, contains all essential amino acids; the leading amino acid is hydroxypyroline. Gelatin contains 84 to 90% by weight protein and 2 to 4% by weight mineral materials, the remainder being water. Gelatin is odorless and practically colorless, insoluble in ethanol, ethers and ketones, but soluble in ethylene glycol, glycerol, formamide and acetic acid. A differentiation is made between two production methods: The acid method for gelatin of the type A and the alkali method for gelatin of the type B. The raw material for type A gelatin (primarily pig skin) is subjected to a three-day decomposition process. When producing type B gelatin, cattle split (center layer between the top grain and hide) or bones are treated with alkali for 10-20 days. The strength of the gelatin is determined by way of a gellometer (texture analyzer) and stated as the bloom value. The isoelectric point of gelatin is at pH 7.5 to 9.3 (type A) and 4.7 to 5.2 (type B).

Gelatin can be chemically modified by reacting primarily the amino groups with mono- or poly-functional reagents such as acylating agents, aldehydes, expoxies, halogen compounds, cyanamides or activated unsaturated compounds, and the properties thereof vary within a broad range. In the present case, the term gelatin encompasses the resulting gelatin derivatives.

The gelatin used according to the invention is highly biocompatible and biocorrodible. The processing can be carried out using standard methods.

For processing, the gelatin is liquefied by heating, such as by way of microwaves, and the is active ingredients are suspended or dissolved. The addition should be carried out prior to gelling, this being the formation of a gel, in particular a hydrogel.

The preparation of the gelatin for coating/filling cavities can be done in buffered solutions. These solutions are particularly easy to process. The pH value of the solutions preferably ranges between pH 5 and pH 8 in order to avoid hydrolysis of the gelatin during processing, which would result in a lower gel strength.

Coating the luminal and abluminal surfaces of the base body of the stent according to the invention with a biocorrodible protective layer comprising gelatin can be done according to known methods, such as the application by spraying, dripping, immersion, condensation, atomization, vapor deposition and/or galvanization.

The layer comprising the gelatin mixture can in particular be present as a gel or hydrogel.

The gel layer may comprise 1 to 20% by weight gelatin mixture, preferably 5 to 10% by weight, wherein the information in % by weight is relative to the total weight of the gel layer.

DETAILED DESCRIPTION

The invention will be explained in more detail hereinafter based on exemplary embodiments.

Figure 1:
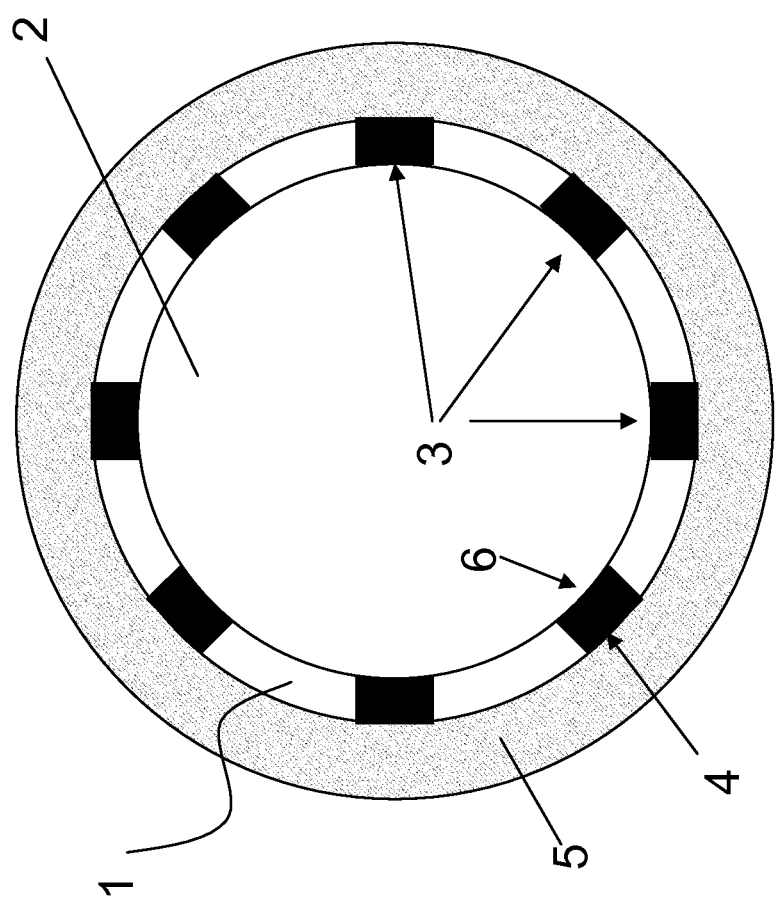
FIG. 1 is a schematic of a cross-section view of a stented vessel section.

FIG. 1 is a schematic cross-section of a vessel section in which one embodiment of the stent according to the invention was implanted. The cutting plane is located perpendicular to the longitudinal axis of the stent. The stent 1 according to the invention delimits a lumen 2 and comprises struts 3, which support the vascular wall 5 with the abluminal sides 4 thereof and adjoin the lumen 2 with the luminal sides 6 thereof.

Figure 2:
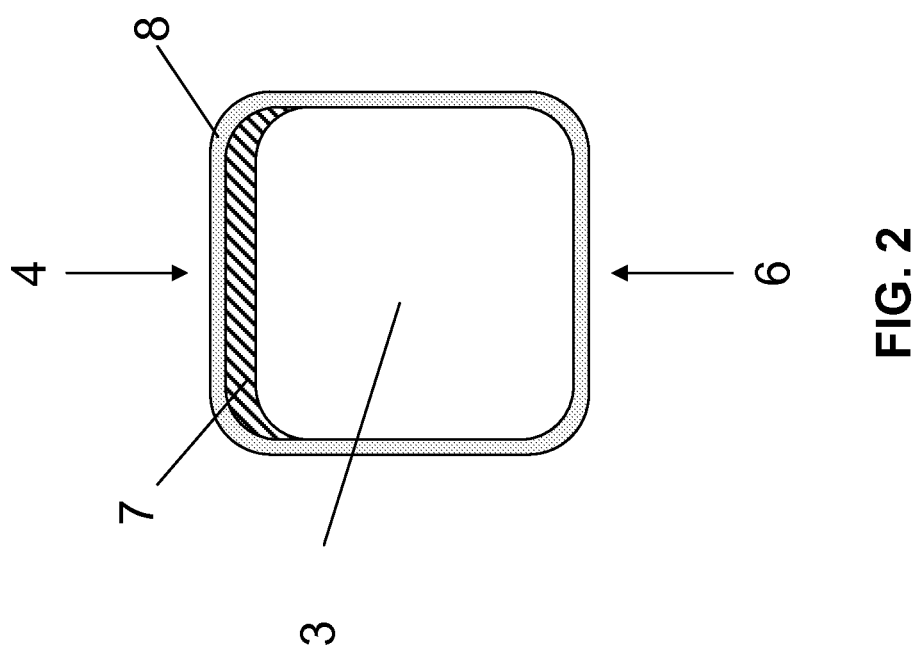
FIG. 2 is a schematic of a cross-section view of a strut of a stent according to the invention.

FIG. 2 shows the cross-section of a strut of a stent according to the invention. At the abluminal side 4, the strut 3 comprises an active ingredient-releasing coating 7. The strut comprises a biocorrodible protective layer 8 both on the luminal side and on the abluminal side carrying the active ingredient-releasing coating 7. The biocorrodible protective layer 8 entirely and form-fittingly covers the luminal and abluminal surfaces of the strut 3. The use of such a biocorrodible protective layer 8 prevents a premature detachment of parts of or the entire active ingredient-releasing coating 7 from the strut 3.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A stent comprising a base body that is made of an implant material, on the abluminal side the base body being covered partially or entirely with an active ingredient-releasing coating, which comprises a polymer and an active ingredient having an antiproliferative effect, characterized in that the base body's luminal surface and the abluminal surface carrying the active ingredient-releasing coating are covered by a biocorrodible protective layer in a form-fitting manner, the biocorrodible protective layer having a congealing temperature lower than body temperature such that heating the protective layer to body temperature liquefies the protective layer to expose the polymer and active ingredient, further wherein the protective layer is pervious to the active ingredient of the active ingredient-releasing coating.

2. The stent according to claim 1, characterized in that the base body comprises the active ingredient-releasing coating exclusively on the abluminal side.

3. The stent according to claim 1, characterized in that the base body of the stent is made entirely or partially of a biocorrodible metallic material.

4. The stent according to claim 3, characterized in that the biocorrodible metallic material is a magnesium alloy.

5. The stent according to claim 1, characterized in that the biocorrodible protective layer comprises or is made of a biocorrodible polymer or a biocorrodible saccharide or biocorrodible gelatin.

6. The stent according to claim 1, characterized in that the biocorrodible protective layer comprises or is made of PLA monomers and PGA monomers.

7. The stent according to claim 1, characterized in that the biocorrodible protective layer comprises or is made of high bloom gelatin, average bloom gelatin or a mixture thereof.

8. The stent according to claim 7, characterized in that the biocorrodible protective layer comprises a gelatin mixture, wherein the gelatin constituents of the gelatin mixture account for 10-90% by weight high bloom gelatin having a gel strength of ≥250 bloom and 90-10% by weight average bloom gelatin having a gel strength of ≥50 to <250 bloom, wherein the information in % by weight is relative to the total weight of the gelatin constituents of the gelatin mixture.

9. The stent according to claim 8, characterized in that the high bloom gelatin has a gel strength of ≥250 to 400 bloom.

10. The stent according to claim 9, characterized in that the high bloom gelatin has a gel strength of 250 to 300 bloom.

11. The stent according to claim 8, characterized in that the gelatin constituents of the gelatin mixture account for 25 to 75% by weight high bloom gelatin and 75 to 25% by weight average bloom gelatin, wherein the information in % by weight is relative to the total weight of the gelatin constituents of the gelatin mixture.

12. The stent according to claim 11, characterized in that the gelatin constituents of the gelatin mixture account for 40 to 60% by weight high bloom gelatin and 60 to 40% average bloom gelatin.

13. The stent according to claim 8, characterized in that the gelatin mixture accounts for 1 to 20% by weight of the biocorrodible protective layer, wherein the information in % by weight is relative to the total weight of the biocorrodible protective layer.

14. The stent according to claim 13, characterized in that the gelatin mixture accounts for 5 to 10% by weight average bloom gelatin.

15. The stent according to claim 1, characterized in that the biocorrodible protective layer comprises a second active ingredient lacking an antiprofilerative effect on endothelial cells and promotes post-implantation stent healing.

16. The stent according claim 1, characterized in that an optional adhesion promoting parylene-containing layer is disposed between the abluminal side of the base body and the active ingredient-releasing coating.

17. The stent according to claim 1, characterized in that the biocorrodible protective layer is configured to corrode at least 50% within 1 day.

18. The stent according to claim 1, characterized in that the active ingredient of the active ingredient-releasing coating is selected from the group consisting of sirolimus, a sirolimus derivative, a taxane, and a taxane salt.

* * * * *